(12) United States Patent
Gamper et al.

(10) Patent No.: US 6,248,059 B1
(45) Date of Patent: Jun. 19, 2001

(54) POWERED EXTERNAL VACUUM APPLIANCE FOR THE TREATMENT OF IMPOTENCE

(75) Inventors: Steven C. Gamper, Atlanta; David S. Rowley, Smyrna; Stephen J. Flynn, Peachtree City; Devin L. Moore, Decatur; John A. McMillan, Atlanta; John M. Mitchell, Martinez; Maureen Carroll, Atlanta, all of GA (US)

(73) Assignee: Timm Medical Technologies, Inc., Eden Prairie, MN (US)

( * ) Notice: Subject to any disclaimer, the term of this patent is extended or adjusted under 35 U.S.C. 154(b) by 0 days.

(21) Appl. No.: 08/646,648

(22) Filed: May 3, 1996

(51) Int. Cl.[7] .................................................. A61F 5/00
(52) U.S. Cl. .............................................................. 600/38
(58) Field of Search ................................. 600/38, 39, 41; 604/346, 347

(56) References Cited

U.S. PATENT DOCUMENTS

| | | |
|---|---|---|
| D. 299,537 | 1/1989 | Morifuji . |
| D. 307,478 | 4/1990 | Morifuji . |
| D. 330,081 | 10/1992 | Walsh . |
| D. 345,420 | 3/1994 | Stewart, Sr. . |
| D. 346,219 | 4/1994 | Fardigh . |
| 2,874,698 | 2/1959 | Sell . |
| 3,744,486 | 7/1973 | Wilson . |
| 4,175,554 | 11/1979 | Gerow . |
| 4,378,008 | 3/1983 | Osbon, Sr. . |
| 4,673,388 | 6/1987 | Schlensog et al. . |
| 4,718,411 | 1/1988 | Stewart . |
| 4,741,329 | 5/1988 | Marcune . |
| 4,753,227 | 6/1988 | Yanuck, Jr. . |
| 4,759,747 | 7/1988 | Aida et al. . |
| 4,813,932 | * 3/1989 | Hobbs ................................. 604/74 |
| 4,856,498 | 8/1989 | Osbon . |
| 4,856,499 | 8/1989 | Kelly . |

(List continued on next page.)

FOREIGN PATENT DOCUMENTS

| | | |
|---|---|---|
| 2658322 | 6/1978 | (DE) . |
| 0148586 | 7/1985 | (EP) . |
| 2129688 | 5/1984 | (GB) . |
| 2155792 | 10/1985 | (GB) . |

OTHER PUBLICATIONS

"Penile Plethysmography of Impotent Men Using Vacuum Constrictor Devices"; by Marmar, et al.; pp. 198–203, vol. XXXII, No. 3; Sep. 1988.
RFSU Vacuumpump Active Erection System Instruction Manual and Product Details; 1991, 11 pages.
"Santoprene" Thermoplastic Rubber Spec Sheet, Undated, 1 page.

Primary Examiner—John P. Lacyk
Assistant Examiner—Rosiland Kearney
(74) Attorney, Agent, or Firm—Merchant & Gould P.C.

(57) ABSTRACT

Pump assisted vacuum therapy impotence treatment apparatus may be provided in either electric or manually operated embodiments. The axis of a pump housing affixed to a vacuum chamber via an elastomeric coupler is at an angle to the vacuum chamber axis, and turned towards a user's torso to be drawn into the user's body for better vacuum sealing. The pump cylinder of a manual embodiment has an enlarged annular rest area for receiving a resilient skirt around the piston head during nonuse of the pump. This prevents compression set of the resilient skirt, for more reliable subsequent use of the pump. The vacuum chamber is tapered and transitions from a relatively smaller round end for receipt of a male sex organ to a relatively larger oval shaped end for bayonet mounting on the resilient coupler. A pair of sizing inserts adjusts the vacuum chamber end which receives the male sex organ. The smaller of the two inserts recesses into the larger insert, which improves the vacuum seal formed with the larger insert. The inserts help reduce scrotal tissue intake.

22 Claims, 9 Drawing Sheets

U.S. PATENT DOCUMENTS

| | | |
|---|---|---|
| 4,883,464 * | 11/1989 | Morifuki ............................ 604/74 |
| 4,886,494 | 12/1989 | Morifuji . |
| 5,020,522 | 6/1991 | Stewart . |
| 5,095,895 | 3/1992 | Walsh . |
| 5,115,800 | 5/1992 | Matejevic et al. . |
| 5,195,943 | 3/1993 | Chaney . |
| 5,213,563 | 5/1993 | Cox . |
| 5,244,453 | 9/1993 | Osbon et al. . |
| 5,421,808 | 6/1995 | Osbon et al. . |
| 5,709,663 | 1/1998 | Younkes ............................ 604/154 |

* cited by examiner

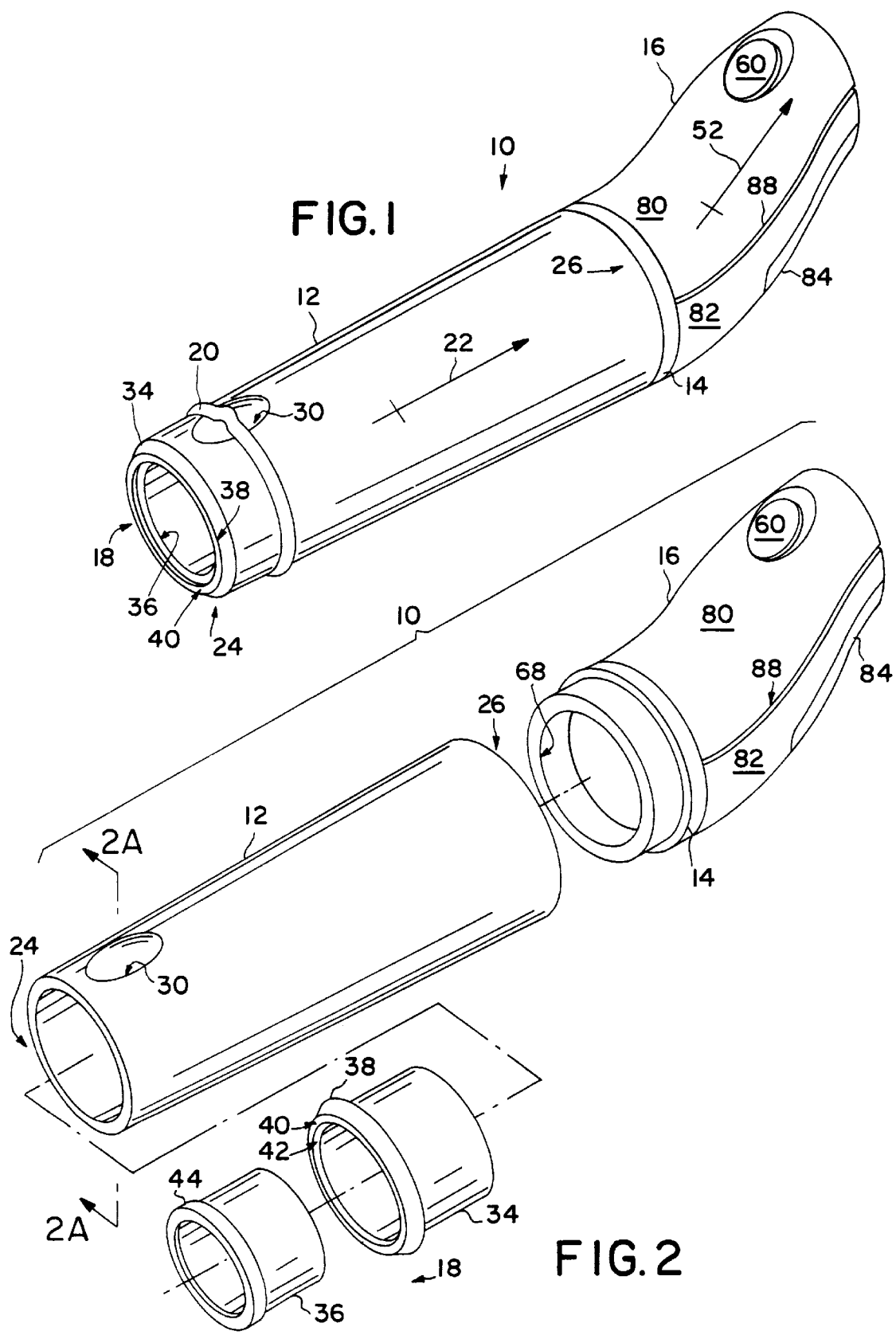

POWERED EXTERNAL VACUUM APPLIANCE FOR THE TREATMENT OF IMPOTENCE

BACKGROUND OF THE INVENTION

Benefit of priority is hereby claimed pursuant to 35 U.S.C. §120 to a prior U.S. design patent application filed under the same title and with the same inventors on Apr. 25, 1996, Ser. No. 29/053,584.

The present invention relates in general to improved impotence treatment appliances and, in particular to pump assisted vacuum therapy impotence treatment technology improved for reliability, performance, and user controlled convenience.

The medical condition of male impotence (i.e., the inability to achieve adequate penile erection for sexual intercourse) has been the subject of significant medical and scientific attention. Various therapies, both surgical and nonsurgical, have been previously made available for treating male impotence. One nonsurgical therapy generally involves the therapeutic use of a vacuum chamber for producing penile engorgement by drawing blood into the erectile bodies of the user's male sex organ, i.e., penis, by using a vacuum. The user's penis is placed within a vacuum chamber or cylinder. With a relative vacuum seal established between the user's body and such vacuum chamber, negative pressure or vacuum is produced within the chamber, leading to vacuum induced engorgement. An elastic cincture band or similar device is then used to secure the engorged condition of the male sex organ.

The art has seen a variety and a progression of devices for use with vacuum therapy. For example, commonly owned U.S. Pat. Nos. 4,856,498 (Osbon) and 4,378,008 (Osbon, Sr.) both disclose examples of vacuum chambers for use in vacuum erection enhancement therapy. In such examples, a vacuum tube is interconnected to a vacuum source (i.e., a source of negative pressure), such as a manual or hand pump. Examples of elastic cincture bands or rings are referenced in such patents. Such rings typically are initially applied to the outside diameter of the vacuum chamber and then subsequently transferred to the base or root of the user's engorged penis. Such arrangement captures and maintains the vacuum induced rigidity thereof.

Different devices and advancements have sought to improve interface of the technology with the user. Commonly owned U.S. Pat. No. 5,244,453 (Osbon, et al.) illustrates a vacuum chamber with a tapered end distal to the user during use. Such built-in taper facilitates application of exemplary cincture bands to the vacuum chamber. Accommodating the relatively small size and strong resiliency of such rings is one aspect of the physical manipulations involved with vacuum enhancement therapy.

The actuation of manually operated vacuum pumps is another existing aspect of the technology. Battery operated vacuum pumps have in some instances been associated with vacuum chambers, such as in direct mount arrangements, as shown by example in further commonly owned U.S. Pat. No. 5,421,808 (Osbon, et al.). There, an inline self-contained housing includes a battery operated vacuum motor apparatus using a reciprocating diaphragm pump arrangement driven by a small electric motor with an eccentric output shaft.

Other arrangements have involved the combination of a hand operated (i.e., manually driven) vacuum pump directly mounted or associated with the vacuum chamber. An example of one such system is the Response system by Smith-Collins Pharmaceutical, Inc., Westchester, Pa., which includes a cylinder which threads onto a vacuum pump, which pump has a long projecting lever pivotably mounted so as to be directed back from an inline pump housing towards the vacuum chamber. See Marmar, et al., "Penile Plethysmography on Impotent Men Using Vacuum Constrictor Devices,"; pp. 198–203; September 1988; Volume XXXII; No. 3; Urology Journal.

Because vacuum therapy impotence treatment requires some physical manipulations, the user's dexterity and strength are inherently involved in the process. With some patients, particularly if advanced age, disease, or other degenerative physical condition is involved, the physical aspects of the therapy may be more significant than with other more generally fit or capable patients. Because of the sensitive nature of the therapy involved, the reliability of any system or technology and its ease of use can be other significant factors in the overall success of the therapy for a given patient.

The disclosures of the above-referenced U.S. patents, and the subject matter of any patents incorporated by reference therein, are fully incorporated herein by reference.

SUMMARY OF THE INVENTION

The present invention addresses various of the foregoing aspects, and others, concerning vacuum therapy impotence treatment operations. Generally speaking, a principal object of this invention is improved impotence treatment appliances and systems. More particularly, one main concern is improved operations involving pump assisted therapeutic devices.

It is another more particular object of the present invention to provide devices having improved reliability and improved user friendliness (i.e., ease of use), to thereby improve overall vacuum therapy success, whether using manually or battery operated pump assisted equipment.

It is a further object to provide devices which result in improved performance, thereby generally increasing user satisfaction, confidence, and abilities in connection with practicing vacuum therapy techniques.

It is another general object to provide apparatus, for use with either electric or manually operated devices, which improves sealing fit and user comfort, for improved efficiency in therapeutic technique and increased user acceptance, thereby again resulting in total overall improvement in practice of the therapeutic technique.

Particularly in connection with presently disclosed manually operated pump embodiments, it is a more specific object to provide improved reliability and dependability in such mechanical vacuum pump arrangements, coupled with improved operating (i.e., stroke) efficiency. It is another more particular object, in the context of either such manually operated embodiments or in electric operated embodiments, to provide a collective self contained system arrangement of predetermined contour and curvature which improves a user's ability to create a vacuum seal between the vacuum chamber and user's body.

Another present specific aspect is to provide an improved vacuum chamber for use alternatively with a variety of devices. Likewise, a more specific present object is to provide improved vacuum chamber inserts alternatively usable with a variety of devices for improved user comfort and improved vacuum seal arrangements.

Additional objects and advantages of the invention are set forth in, or will be apparent to those of ordinary skill in the art from, the detailed description which follows. Also, it should be further appreciated that modifications and variations to the specifically illustrated and discussed features or materials and devices hereof may be practiced in various embodiments and uses of this invention without departing from the spirit and scope thereof, by virtue of present reference thereto. Such variations may include, but are not limited to, substitution of equivalent means and features or materials for those shown or discussed, and the functional or positional reversal of various parts, features, or the like.

Still further, it is to be understood that different embodiments, as well as different presently preferred embodiments, of this invention may include various combinations or configurations of presently disclosed features or elements, or their equivalents (including combinations or configurations thereof not expressly shown in the Figures or stated in the detailed description). One exemplary such embodiment of the present invention relates to a male organ conditioning appliance for the treatment of impotence. Such an appliance may comprise an elongated vacuum chamber and a combination self contained pump housing and chamber handle.

Such an elongated vacuum chamber preferably has a first open end adapted for introduction of a user's flaccid penis into the chamber. There is also a second open end for application of negative pressure to the chamber adequate so as to produce an erection in the user's flaccid penis. Such vacuum chamber preferably has a generally longitudinal axis.

The foregoing combined housing and handle is intended to be associated with the vacuum chamber second open end for application of negative pressure thereto. The combined housing and handle has a generally longitudinal axis which is disposed at a predetermined angle relative to the vacuum chamber axis. Such angled axis is pitched upwardly towards the user's torso so as to facilitate drawing in of the appliance to the user's body for a vacuum seal with the vacuum chamber first open end during use of the appliance.

In the foregoing arrangement, the appliance may be embodied with either a manually operated pump and external pump lever or a battery operated pump and an external power switch. One or more additional features may be practiced in alternative combinations or arrangements, such as an elastomeric coupler for interfacing between the vacuum chamber and combination housing and handle, venting means for selectively venting the vacuum chamber, insert means for adjusting the size of the vacuum chamber first open end, and resilient cincture band means for capturing a user's erection.

Another present exemplary embodiment concerns a pump assisted vacuum therapy impotence treatment system with separable components to facilitate storage and cleaning of such components. Such a system preferably may comprise a vacuum chamber generally similar to that described above (with possible additional features), a coupler, a pump housing, a vacuum pump, and venting means.

Such a coupler may be formed of resilient material and have a generally oval shaped interference fit mount for sealing fit thereof with a generally oval shaped second open end of the vacuum chamber. The pump housing as referenced has a predetermined contour and is integrally associated with the coupler. The contour is such that the axis of the housing is at a predetermined angle to the longitudinal axis of the vacuum chamber.

A selectively operable vacuum pump is received in the foregoing pump housing and has pump actuation means situated externally of such housing for selective user actuation. When so actuated, the vacuum pump produces negative pressure within the vacuum chamber (of course, assuming that the vacuum chamber is associated with the coupler). Venting means are operatively associated with the pump housing and selectively actuated by a user for selectively venting negative pressure in such vacuum chamber. Such venting facilitates removal of the vacuum chamber from a user's body.

Yet another construction comprising a present exemplary embodiment includes a self contained manually operated male organ conditioning appliance, preferably comprising an elongated vacuum chamber (generally such as described above) and a self contained manually operated pump housing removably associated with the vacuum chamber second open end.

Such a pump housing preferably includes a vacuum pump with a pump lever extending therefrom to be accessible for selective user actuation.

The foregoing exemplary vacuum pump preferably includes a piston having a piston head with a circumferential resilient skirt for sealing against a cylinder wall and for creating a vacuum within such cylinder as the position of the piston is manipulated. The vacuum pump further includes a cylinder having a first predetermined inside diameter and a defined annular rest area for the piston skirt. Such rest area has a slightly enlarged inside diameter relative to the first predetermined inside cylinder diameter. With the rest area receiving the piston resilient skirt whenever such piston is at an at rest position thereof, compression set of the resilient skirt is prevented. This enables the skirt to make subsequent movement within the cylinder with continuing interference fit with the cylinder inside diameter, even after periods of nonuse of the vacuum pump. In other words, the pump continues to operate successfully rather than having a gap between an undesirably radially compressed resilient skirt and the cylinder inside diameter with which it must function in order to create negative pressure.

Examples of other features which may be alternatively combined with the above arrangement may relate to providing a predetermined angle between the housing and vacuum chamber axes, mounting of the pump lever so as to pivot away from a user's body, and providing venting means for the vacuum chamber.

Still further aspects of the subject invention may relate to other vacuum therapy related features. For example, an improved vacuum chamber in accordance with the present invention may comprise a generally elongated tube having a relatively smaller first open end adapted for introduction of a user's flaccid penis into the tube, and a generally larger second open end for application of negative pressure to such tube. Such first open end may be generally round and adapted for receipt of a sizing insert therein and for receipt of a resilient cincture band therearound, while the second open end may be generally oval shaped. With such an arrangement, the vacuum tube forms a reducing taper from the second open end towards the first open end, and also transitions therealong from the generally oval shape to the generally round shape.

Still further, improved sizing inserts may be provided in accordance with the subject invention for use with an open end of an elongated vacuum chamber of such type as used with pump assisted vacuum therapy, to permit selective altering of the size of the inside diameter of the vacuum chamber open end. Such an arrangement facilitates obtaining a vacuum seal between the vacuum chamber open end and the user.

Such exemplary improved sizing inserts may comprise a combination of a primary annular insert and a secondary annular insert. Such primary insert may be adapted for receipt in the vacuum chamber open end, and have a radially outward extending flange on one end thereof to abut the vacuum chamber open end when introduced thereto. Such arrangement forms a user contact surface outside of the vacuum chamber for forming a seal between the vacuum chamber and user. Such primary annular insert may further have at least one inside diameter radially inward projection separated from the user contact surface. The secondary annular insert may be adapted to be selectively received within the primary one. It may have a radially outward projecting flange on one end thereof for forming an interference fit with the inside diameter projection of the primary annular insert. With such an arrangement, the flange of the secondary annular insert is recessed below the user contact surface and removed away from primary user contact, so that the seal between the user and the vacuum chamber open end is always maintained by the primary annular insert.

Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended Figures, in which:

FIG. 1 is a generally side and top perspective view of an exemplary system in accordance with the subject invention, in an assembled condition, and utilizing an electric operated vacuum pump arrangement;

FIG. 2 is a generally side and top perspective view of the exemplary embodiment of present FIG. 1, in an exploded arrangement thereof, separately showing various components;

Figure 2A:
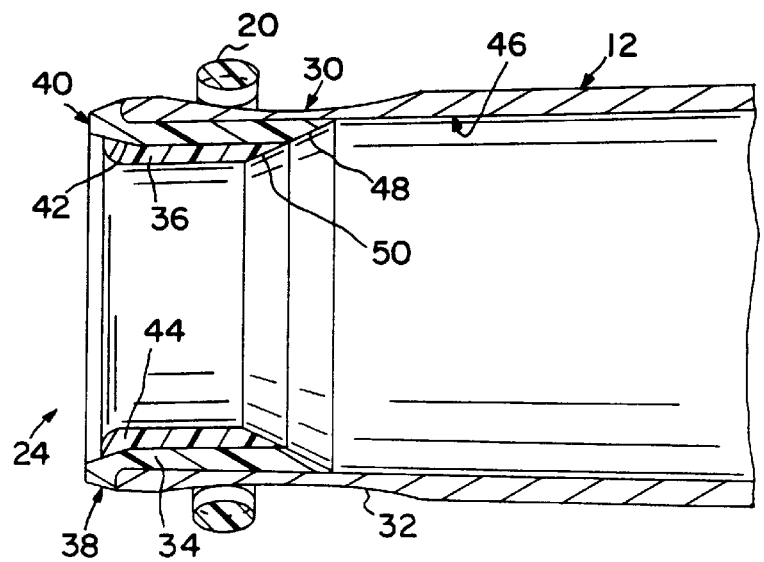
FIG. 2A is an enlarged cross sectional view of a portion of the vacuum chamber and insert means embodiments illustrated in present FIG. 2, taken along section line 2A—2A indicated therein.

Repeat use of reference characters throughout the present specification and appended drawings is intended to represent same or analogous features or elements of the invention.

DETAILED DESCRIPTION OF THE PREFERRED EMBODIMENTS

The present invention relates to various aspects of impotence treatment systems, including different embodiments of various separable components and combinations thereof as illustrated and represented throughout the present Figures. As discussed in greater detail herein, some present exemplary embodiments involve use of electric operated vacuum pumps while others involve various manually actuated vacuum pumps. Other present features focus on different therapeutic components, such as the configuration of the vacuum chamber, removable sizing inserts usable therewith, and combinations of pump housings and vacuum chambers resulting in improved therapeutic practices and results. All such variations and alternative features are intended to come within the spirit and scope of the subject invention.

FIGS. 1 and 2 illustrate assembled and exploded views, respectively, of an exemplary pump assisted vacuum therapy impotence treatment system generally 10 in accordance with the subject invention, having separable components to facilitate storage and cleaning thereof. Referring collectively to such two Figures, an exemplary vacuum chamber generally 12 cooperates with a coupler 14, which in turn is associated with a pump housing generally 16.

Insert means generally 18 are operatively associated with vacuum chamber 12 for adjusting the size of the entrance thereto. Such adjustment, when appropriately made, facilitates both user comfort and vacuum sealing between such chamber and the user's body during vacuum therapy use thereof.

Resilient cincture band means generally 20 may be selectively received about the vacuum chamber adjacent an end thereof, for subsequent application to the base of a user's penis to secure an engorged condition thereof. Additional details regarding resilient cincture band means form no particular aspect of the subject invention, which details are otherwise set forth additionally in examples included in the above-referenced patents, incorporated by reference into the present application.

Referring to FIGS. 1, 2, 2A, and 12 through 15, vacuum chamber generally 12 in accordance with the subject invention preferably comprises a transparent plastic or equivalent material generally longitudinal tube, having a longitudinal axis generally 22 (FIG. 1). Chamber 12 has a first open end 24 which is generally circular and adapted for introduction of a user's flaccid penis (i.e., proximal to the user). A second open end generally 26 thereof is generally oval shaped and adapted for introduction of negative pressure to vacuum chamber 12 (i.e., distal to the user), as originating from pump housing 16 via coupler 14.

Referring more specifically to the above-referenced Figures concerning vacuum chamber 12 in accordance with the subject invention, it will be readily apparent to those of ordinary skill in the art from the present disclosure that vacuum chamber 12 is generally tapered, going from the relatively smaller first end 24 to the relatively larger second end 26. Also, as illustrated, the vacuum chamber transitions from the generally round shape at end 24 to the generally oval shape at end 26. In addition to the aesthetic aspects of such arrangement as will be apparent to those of ordinary skill in the art, specific features herewith facilitate use of vacuum chamber 12 with additional components, such as insert means 18 and/or cincture band means 20, and also facilitate interface with the particular self contained pump housing 16 in accordance with the subject invention (whether involving electrical or manually operated pump mechanisms).

Also, it occurs with some users that the male sex organ will move or otherwise be laterally deflected during the course of the erection process, and the overall enlarging taper (from end 24 towards end 26) and the additional internal space afforded by transitioning from circular to oval shape, collectively improves therapeutic technique. Specifically, there is additional room within the chamber without engagement of perhaps sensitive, engorged areas of the male sex organ with solid objects such as the vacuum chamber inside diameter.

Figure 13:
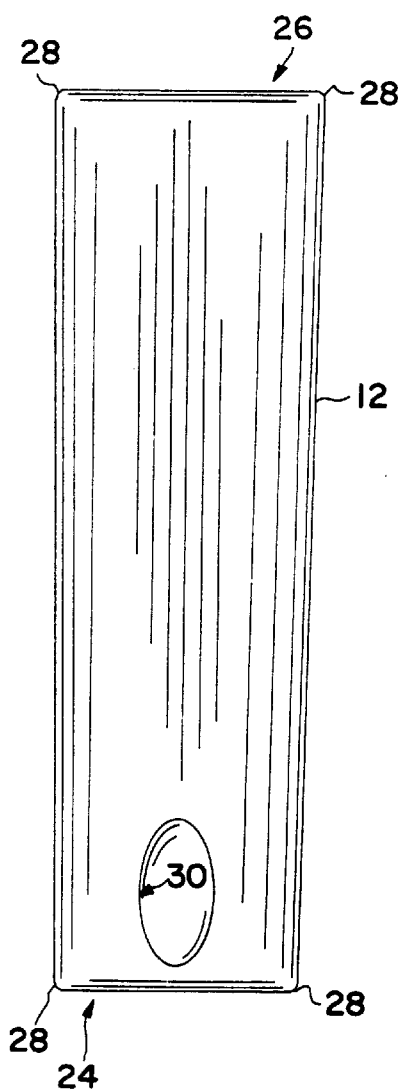
FIG. 13 is a generally top elevational view of the exemplary vacuum chamber of FIG. 12 in accordance with the subject invention, which view is identical to the bottom elevational view thereof, and which view is rotated for alignment: with the same rotational position as that of FIG. 12.
Figure 14:
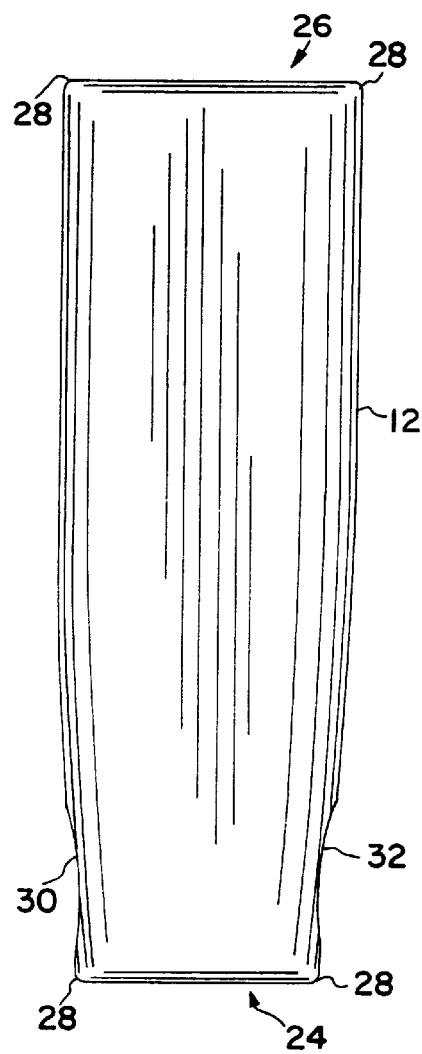
FIG. 14 is a side elevational view of the exemplary embodiment of the vacuum chamber of present FIGS. 12 and 13 (which view is identical on either the left or right side thereof), which represents such vacuum chamber rotated along its longitudinal axis 90 degrees from the position thereof illustrated in present FIG. 13.
Figure 15:
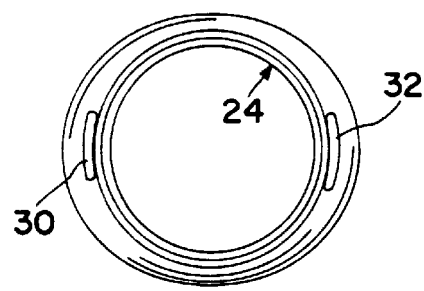
FIG. 15 is a generally end elevational view of a proximal or first open end of the exemplary vacuum chamber of present FIGS. 12 through 14, rotated for alignment with the same rotational position as that of present FIG. 14.

While various features may be practiced in accordance with such a present vacuum chamber 12, it is preferred that each end 24 and 26 be provided with relatively rounded edges generally 28 (as better illustrated in present FIGS. 13 and 14). First end 24 is also adapted for receipt of a sizing insert, such as insert means 18 therein (discussed in greater detail below). End 24 is also particularly adapted for receipt of a resilient cincture band, such as band means 20 therearound (see FIG. 1). Those of ordinary skill in the art will understand and appreciate that such band may assume various shapes, and may be placed in various manners onto or about vacuum cylinder 12, for subsequent application to the root of a user's male sex organ to secure an engorged condition thereof. Different forms of band means 20, as referenced above, or as otherwise provided, may be utilized in conjunction with other present features.

Vacuum chamber generally 12 may preferably be provided with at least one registration element formed such as a depression 30 in the outside diameter of the generally elongated tube relatively adjacent open end 24 thereof. Such a registration element 30 facilitates user alignment of the vacuum chamber during the erection process, and facilitates receipt and alignment of band 20 about the tube first open end. See also FIG. 2A.

As further represented by present FIG. 2A, a pair of such registration elements may include a second depression generally 32 (see also FIGS. 14 and 15) formed in diametrically opposite areas of the outside diameter of chamber 12. While various shapes may be practiced, as illustrated, such depressions 30 and 32 are preferably generally oval, such as with a length in a range of from about 1.2 inches to about 1.5 inches and a width in a range of from about 0.3 inches to about 0.6 inches.

As represented also in FIG. 2A, chamber 12 may have a wall thickness preferably in a range of from about 0.1 inches to about 0.2 inches. Likewise, other dimensions of vacuum chamber 12 may be varied in accordance with the subject invention. For example, the generally elongated tube may have a total length in a range of from about 8 inches to about 10 inches. First open end 24 may have a generally round inside diameter of about 2 inches (with some variation permitted); and second open end 26 may have a generally oval inside diameter of about 2.5 inches by 2.25 inches (again with some variation permitted).

Other aspects of the present invention relate to improved sizing inserts or insert means generally 18, such as represented, for example, in present FIGS. 1, 2, and 2A. The operational efficiency of any vacuum therapy device depends greatly on the quality of the vacuum seal obtained between the apparatus (i.e., the vacuum chamber) and the patient (i.e., user). If a poor quality vacuum seal is obtained, either due to a continuously low sealing effect, or due to an intermittent significant leakage problem, the entire vacuum therapy may be frustrated. Alternatively, if not actually failing, the user may experience personal frustrations (for example, delays) which lead ultimately to dissatisfaction with the therapy. Thus, a quality vacuum seal between appliance and user is an important consideration.

Another aspect of the quality of the vacuum seal relates to the fit between the user's anatomical size and the opening of the vacuum chamber. It is well known that the size of the male sex organ varies from one user to another, with no particular size being average or "normal." Accordingly, adjustment of the equipment for a closer approximation to a particular user's anatomy is important. If the opening is physically too small, it will be difficult to properly achieve full erection or engorgement, and subsequently comfortably remove the appliance from the cinctured penis. On the other hand, if the equipment opening is too large relative to the user's anatomy, poor vacuum sealing may occur. Another potential in such instance is undesired vacuum intake, such as intake of excessive amounts of pubic hair (causing potential discomfort during application of the cincture band), or even scrotal tissue intake. A proper fit tends to help alleviate all of the above undesired possibilities.

In some instances, the inside diameter of vacuum chamber open end 24 may fit appropriately, without any sizing insert. In other instances, the use of one or more inserts may be desirable. In the insert means 18 presently disclosed, improved sizing inserts for use with open end generally 24 of elongated vacuum chamber 12 are designed for use with pump assisted vacuum therapy impotence treatments, by selectively altering the size of the inside diameter of the vacuum chamber open end to facilitate obtaining a vacuum seal between such end and the user. Such improved sizing inserts may comprise a pair of annular inserts, including a primary or larger insert generally 34 and a secondary or relatively smaller insert generally 36.

Primary annular insert 34 is generally adapted for receipt in vacuum chamber open end 24. It has a radially outward extending flange 38 on one end thereof which abuts the vacuum chamber open end 24 as insert 34 is introduced into chamber 12. The surface or face generally 40 which results from such an arrangement faces the user and forms a user contact surface outside of vacuum chamber 12. Such surface 40 forms a seal between the vacuum chamber and the user.

Primary annular insert 34 further has at least one inside diameter radially inward projection generally 42. Projection 42 preferably comprises an annular angled ridge (see FIG. 2A), and is separated (i.e., recessed) from the user contact surface 40. Secondary annular insert generally 36 is then adapted to be selectively received within primary annular insert 34. Insert 36 has a radially outward projecting flange generally 44 on one end thereof. Flange 44 forms an interference fit with the inside diameter projection or annular angled ridge 42 of insert 34. As illustrated by FIGS. 1 and 2A, the resulting positioning of insert 36 relative to insert 34 is such that the flange 44 of insert 36 is recessed below user contact surface 40. Hence, any seal between the user and vacuum chamber open end 24 is always maintained by the primary annular insert 34, and always constitutes the user contact surface 40.

As better and further represented by present FIG. 2A, the angled flange 44 of insert 36 mates for sealing against annular angled ridge 42 of insert 34, so as to seal against any air leakage between the primary and secondary annular inserts 34 and 36, respectively. With the foregoing arrangement, use of a second sizing element is not accompanied by any air loss or leakage due to the insert arrangement.

Another aspect of insert means 18 is that such inserts are preferably formed of resilient material having a relatively medium range hardness rating. One example of an acceptable material is a thermoplastic rubber having a hardness rating of about 40 Shore D, such as sold under the brand name "Santoprene", available from Advanced Elastomeric Systems of Akron, Ohio. It has been found that such a choice of material provides a desirable result, in that it is soft enough to afford a desired comfort level when pressed against a user's body, but is hard enough to help form a desired vacuum seal.

Still another aspect of the subject invention relates to the sizing and dimensions of the subject inserts 34 and 36. For example, primary annular insert 34 preferably projects along its axial length at least about 1 inch into the inside diameter of vacuum chamber 12, as represented by present FIG. 2A. Such an arrangement helps comprise a guard against the drawing in of scrotal tissue into contact with the inside diameter generally 46 of vacuum chamber 12. Also, should scrotal or penile tissue come close to the juncture between inserts 34 and 36 and the vacuum chamber inside diameter 46, tapered regions 48 and 50 respectively are provided to prevent any tissue entrapment or contact damage.

Lastly, the thicknesses or sizes of the insert walls may be varied so as to likewise vary the adjustment achieved by use thereof. Wall thicknesses or widths in a range of from about 0.1 inches to about 0.15 inches are preferred exemplary embodiments.

It will be appreciated that the features of the above-discussed insert means 18 may be practiced in accordance with the subject invention in combination with a vacuum chamber such as exemplary chamber 12 herewith, or with other vacuum chambers, having generally circular ends for receipt of a user's penis. Likewise, present combinations may include use with other forms of vacuum pumps or means for generating negative pressure within an associated vacuum chamber. Still further, various resilient cincture band rings or other features may be combined with or in use of any such embodiments or systems, all of which is intended to come within the spirit and scope of the present invention.

FIG. 1 represents another aspect of the subject invention, in that it reflects a combination of an elongated vacuum chamber with a contoured or particular predetermined angled pump housing 16. As represented in present FIG. 1, element 16 may alternatively be regarded as comprising a combination self contained pump housing and chamber handle, inasmuch as it becomes integrally associated with vacuum chamber 12 (optionally through coupler 14), whereby the user may manipulate chamber 12 by manipulating component 16, ultimately leading to the production of negative pressure in chamber 12 for application to the user's male sex organ.

Figure 3:
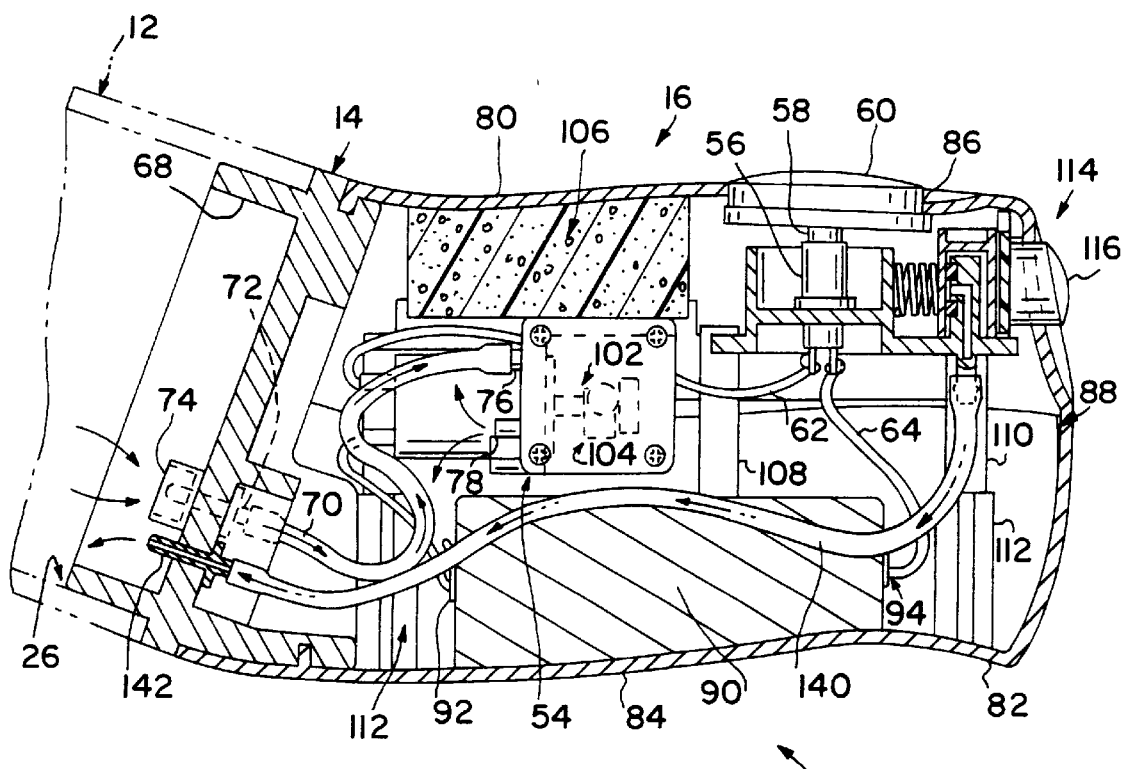
FIG. 3 is an enlarged longitudinal cross sectional view of the pump housing and internal features of the exemplary electric operated embodiment represented in present FIGS. 1 and 2, with an exemplary vacuum chamber partially illustrated in dotted line to show position thereof.

An additional feature reflected by present FIG. 1 is that such combined housing and handle 16 has a generally longitudinal axis, such as represented by arrow 52, which is disposed at a predetermined angle relative to the vacuum chamber generally longitudinal axis 22. Those of ordinary skill in the art will appreciate that an exact angular measurement in such FIG. 1 is not intended between arrows 52 and 22 since FIG. 1 shows a generally perspective view, which somewhat distorts the angularity in appearance. FIG. 3 (a view from a side) shows more directly the subject angle. However, it will be well understood that end 24 of chamber 12 during use thereof is directed towards and in contact with a user's body, with chamber 12 otherwise projecting generally horizontally away from the user (assuming a standing position of the user). Thus, as represented in present FIG. 1, housing (or combined housing and handle) component 16 is disposed at a predetermined angle relative vacuum chamber 12 such that it is pitched upwardly towards the user's torso.

With the user grasping component 16, such an upturned angle facilitates the drawing in of the appliance 10 to or towards the user's body for a vacuum seal with end 24 (or user contact surface 40 if insert means 18 are used) during use of appliance or system 10. It is not uncommon that one of the particular manipulations which may be somewhat problematic for some users is to achieve adequate inward pressure to create and maintain a proper vacuum seal. To such extent, the arrangement represented by present FIG. 1 provides a considerable improvement in the ability of a particular user to manipulate apparatus 10 for achieving a desired level of inward pressure for an adequate vacuum seal, while also facilitating operation of such equipment and conduct of the vacuum therapy technique.

While FIG. 1 represents an electric powered embodiment of the subject invention, it is to be understood that such an angled housing component 16 may be practiced in conjunction with manually operated embodiments thereof, such that the advantageous predetermined angle between axes 52 and 22 is again provided for all such embodiments. It is to be further understood that such predetermined angle may be varied, and for example fall in a range of from about 10 degrees to about 30 degrees. In some instances, such range may be from about 15 degrees to about 25 degrees, depending on the structure of the components otherwise utilized. In the exemplary embodiment of present FIG. 1 (and other illustrated embodiments herewith), an exemplary preferred predetermined angle is illustrated of about 20 degrees.

Referring to FIGS. 1, 2, 3, 4A, and 4B, it is represented that the combination housing and handle generally 16 may include a battery operated pump generally 54 and an external power switch 56 for such pump 54. Power switch 56 may be of the momentary (or dead man) type contact, as well known to those of ordinary skill in the art. Upon depression of a plunger 58 via for example an external button cover 60, a circuit is closed through electrical wires 62 and 64 to operate pump 54.

As shown by all such Figures, and especially by FIGS. 1 and 2, such button cover 60 is readily accessible to a user so as to be selectively actuated, such as by the user's thumb, whenever arrangement 10 is received into the proper position relative to user's body. In essence, button 60 cooperating with power switch 56 comprise pump actuation means external to housing 16.

Figure 10:
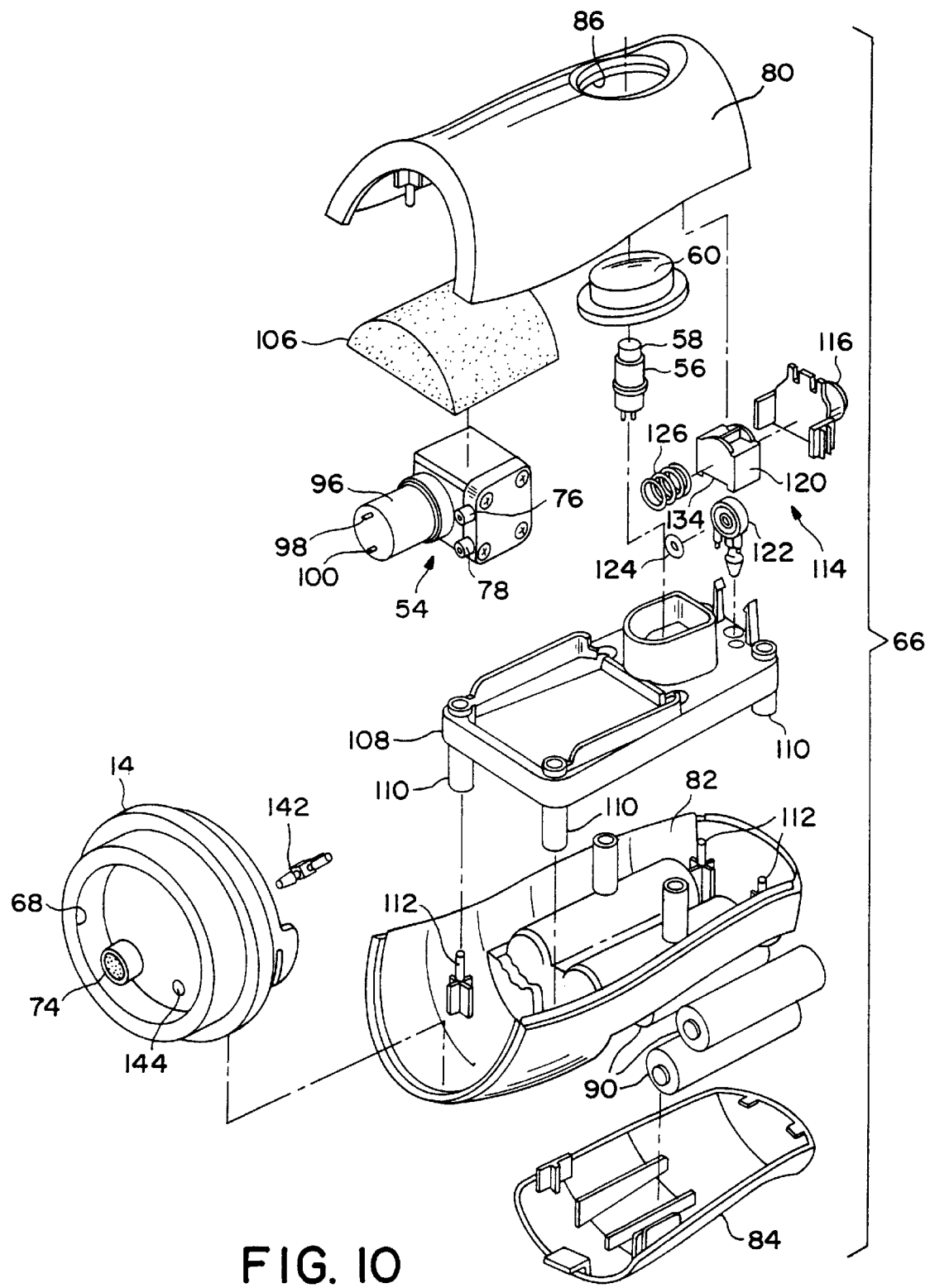
FIG. 10 is an exploded view, with component details, of the exemplary electric operated embodiment as otherwise represented in FIGS. 1 through 4B.

FIGS. 3 and 10 illustrate additional details of an exemplary battery operated self contained arrangement generally 66 in accordance with the subject invention. More specifically, FIG. 3 illustrates a generally longitudinal cross sectional view of such arrangement 66, while FIG. 10 illustrates an exploded, component detail view thereof.

More specifically, coupler 14 is illustrated as having a generally oval shaped interference fit mount generally 68 for sealing fit thereof with the vacuum chamber 12 generally oval shaped second open end 26 thereof. Preferably, coupler 14 is formed of a resilient material, such as a rubberized material over-molded or otherwise fitted onto housing 16. The resulting interference between housing 16 and coupler 14 (as well shown in the cross sectional view of FIG. 3), and the subsequent bayonet type interference fit between element 68 and end 26, enable an effective controlled vacuum environment between pump 54 and the interior of vacuum chamber 12.

Of course, additional tubing (hermetically sealed) is included between pump 54 and the interior of vacuum chamber 12. Specifically, a sealed air tube 70 is hermetically associated with a barb or similar 72, which cooperates with a filter 74 (such as formed of resilient foam or the like) for interconnecting the vacuum input generally 76 of pump 54 with the interior of vacuum chamber 12. As shown by the solid line arrows in FIG. 3, air flows from vacuum chamber 12 (generating a negative pressure therein) into pump 54 and out exhaust port 78 thereof. From port 78, the exhausted air variously vents into the ambient surroundings.

As represented by FIGS. 1, 2, 3, and 10, housing 16 may generally comprise an upper housing member 80 and lower housing member 82, with other features such as a removable battery cover 84, and opening 86 for passage of button cover 60, and a seal line generally 88 between the two housing portions. Such sealed line may be joined by epoxy or similar closures, intended as a permanent seal, or with other means such that the housing elements 80 and 82 are more readily removable from one another.

As represented in the various Figures, different alignment studs and receivers or their equivalents may be provided within the interior of housing elements 80 and 82 for joinder thereof, or for the securement and placement of components and members within housing 16. Such features will be well understood by those of ordinary skill in the art from the remaining disclosure herewith, including the present Figures, without detailed discussion thereof. Additional details of some such aspects of the subject invention are set forth in further discussion herein.

A number of batteries 90 (such as three AA batteries) may be provided within housing 16 inside removable battery door 84. Those of ordinary skill in the art will appreciate the necessary electrical connections (presently represented by elements 92 and 94) which must be provided to selectively complete an electrical circuit via momentary switch 56 and wiring 62 and 64 with electric actuated pump 54 (and including batteries 90).

Pump 54 is provided with a small electric motor generally 96, having electrical contacts 98 and 100 (which are part of the above referenced circuit connections). When operating, electric motor 96 utilizes an eccentric output shaft generally 102 for operating a movable diaphragm pump mechanism generally 104, as well understood by those of ordinary skill in the art, and particular details of which form no particular aspect of the subject invention. An electrically operated or actuated pump system as represented and as disclosed in U.S. Pat. No. 5,421,808 (fully incorporated herein by reference, including all U.S. patents referenced therein) may be practiced in accordance with the subject invention, or other embodiments may be practiced for generating a vacuum intake at port 76 and vacuum exhaust at port 78.

A resilient foam element generally 106 may be incorporated into housing 16 to provide a dampened support element for pump arrangement 54. Additional mounting features will be apparent to those of ordinary skill in the art from the remainder of the disclosure herewith (including the present Figures), or as otherwise understood. For example, a battery removal ribbon (not shown) may be included in the opening accessed by removal of battery door 84, to facilitate removal of batteries 90.

Figure 4A:
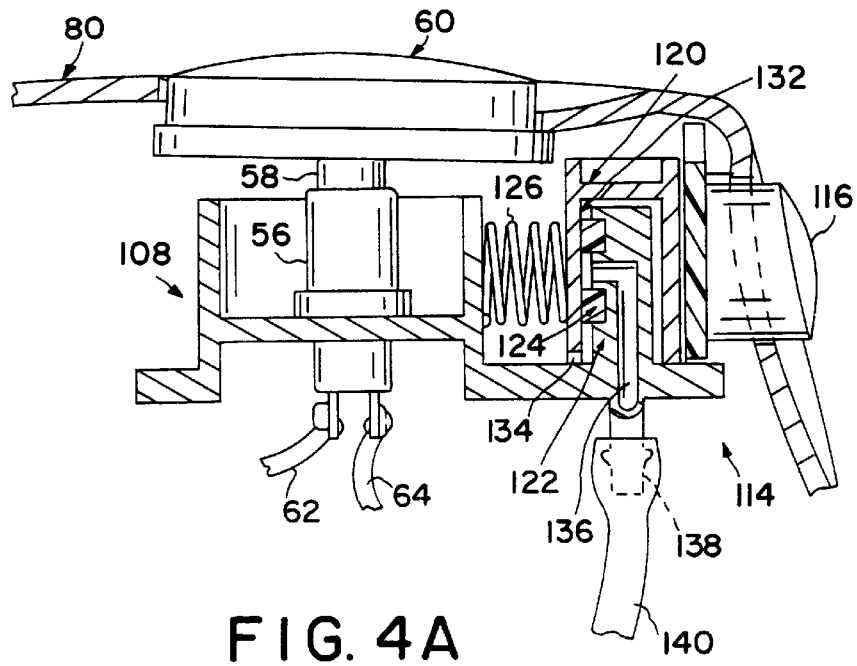
FIG. 4A is a greatly enlarged view of actuation means of the electric operated exemplary embodiment of present FIGS. 1, 2, and 3, and generally of venting means in accordance with the subject invention for use with any embodiment thereof (electric or manual) for venting negative pressure from the vacuum chamber, all of which illustration is primarily shown in cross sectional view.
Figure 4B:
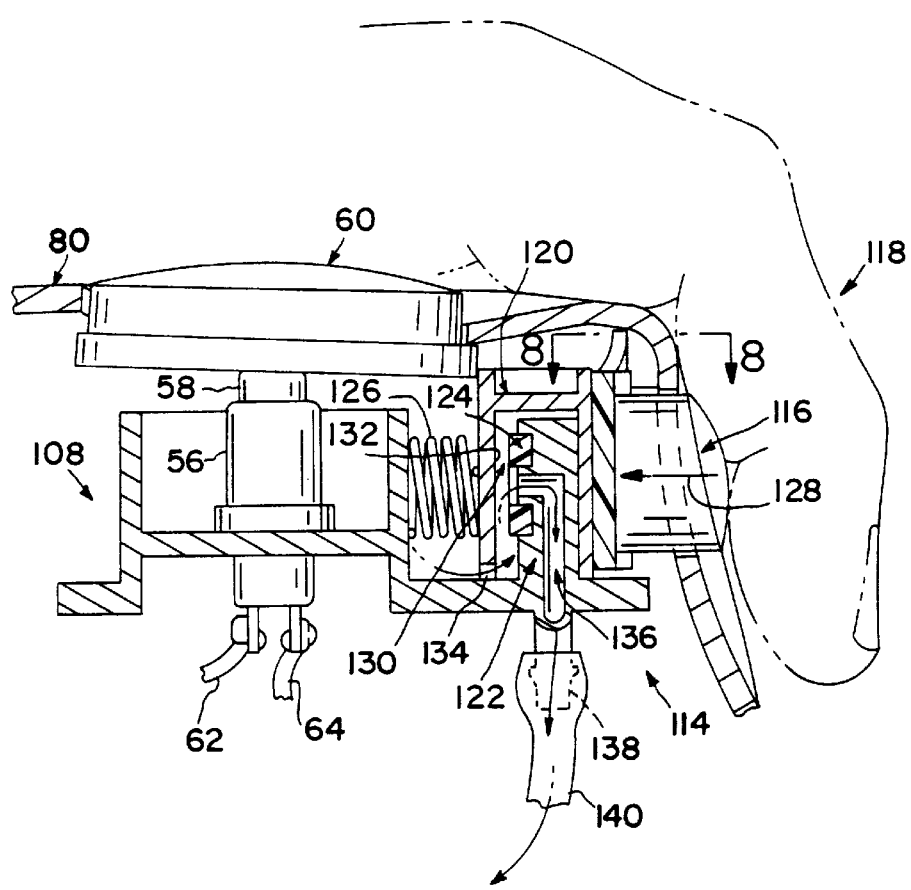
FIG. 4B illustrates the identical features as illustrated in present FIG. 4A, further representing user actuation of the venting means thereof.

A chassis generally 108 may be internally included within housing 16, such as supported with female elements generally 110 received onto support spikes 112, for mounting and support of additional elements. For example, venting means generally 114 may be supported by various aspects of internal chassis generally 108. FIGS. 4A and 4B show enlarged detail of venting means 114 in accordance with the subject invention, including the unactuated and actuated positions thereof, respectively. A much smaller illustration (in unactuated position) is illustrated in the longitudinal cross section of present FIG. 3, and an exploded view of such features of venting means 114 is represented in present FIG. 10.

It is to be noted that similar or near identical venting means may be utilized in either electric or manually operated embodiments of the subject invention. Accordingly, similar or corresponding elements between the electric and manually operated embodiments are provided with corresponding reference characters, without requiring additional discussion thereof.

Figure 8:
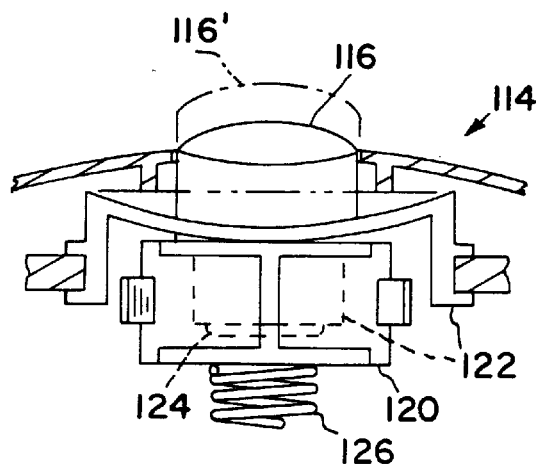
FIG. 8 is an enlarged sectional view of a portion of the exemplary venting means (usable with either electric or manually operated embodiments) as represented in present FIG. 4B, taken along the view line 8—8 indicated therein.

Referring more particularly to such venting means, it is apparent from present FIGS. 3, 4A, 4B, and 10 that a vent button generally 116 is provided relatively externally to housing 16, for selective actuation by a user, such as represented by the interaction of representative finger 118 in present FIG. 4B. As indicated in such FIG. 4B by view line 8—8, a further view of components or portions of venting means generally 114 is represented in such FIG. 8. The solid line positions of FIG. 8 represent an actuated position of vent button 116, while the broken line illustration thereof (116') represents an unactuated position thereof.

Referencing FIGS. 3, 4A, 4B, 8, and 10, venting means 114 further includes a vent stem generally 120, a vent body generally 122 (shown in dotted line in FIG. 8), a vent O ring generally 124 (shown in dotted line in present FIG. 8), and a vent spring generally 126.

As perhaps better shown by present FIGS. 4A and 4B, vent spring 126 normally biases vent stem 120 towards the right (per the orientation of such Figures), which brings an interior surface 132 of such vent stem into sealing contact with vent O ring 124 (see FIG. 4A). Whenever vent button 116 is depressed generally in the direction of arrow 128 (see FIG. 4B), the bottom side of vent button 116 engages vent body 120, and pushes it also in the direction of arrow 128, thus opposing (and compressing) biasing spring 126 (FIG. 4B). This causes a gap generally 130 (FIG. 4B) to be formed between O ring 124 and the interior surface 132 of vent stem 120. An undercut or passage generally 134 of vent body 120 then permits an air flow via internal channel 136. Such air flow is interconnected in a hermetic seal via barb 138 to a vent line or tubing 140.

The following traces system air flow through a venting operation. Available ambient air is used during venting. Generally, it is at local atmospheric pressure and has no relative negative pressure. As better illustrated in present FIG. 3, such ambient air vented by venting means 114 passes through vent tube 140 via barb 142 and passage 144 (formed through coupler 14) into the negative pressure environment otherwise existing within the interior of vacuum chamber 12. Therefore, selective depression or actuation of vent button 116 (FIG. 4B) results in the air flow indicated by the flow arrows associated with tube 140 and venting means 114 in FIGS. 4B and 3, so as to vent negative pressure in (i.e., supply air to) vacuum chamber 12. The resulting reduction of negative pressure permits selected removal of the vacuum appliance from the user's body (i.e., permits the user's penis, in engorged condition, or otherwise, to be withdrawn from vacuum chamber 12).

It is to be further understood by those of ordinary skill in the art that a natural vacuum limitation or vacuum limiter feature is built into the electric embodiment arrangement 66, by virtue of the vacuum limit of pump arrangement 54. In other words, the pump arrangement 54 has a known limit or ability (such as 16 inches of mercury) of the vacuum which it can draw within vacuum chamber 12. The mechanical actuated embodiments discussed below have other vacuum limiter means in accordance with the subject invention, to perform a similar function.

Figure 5:
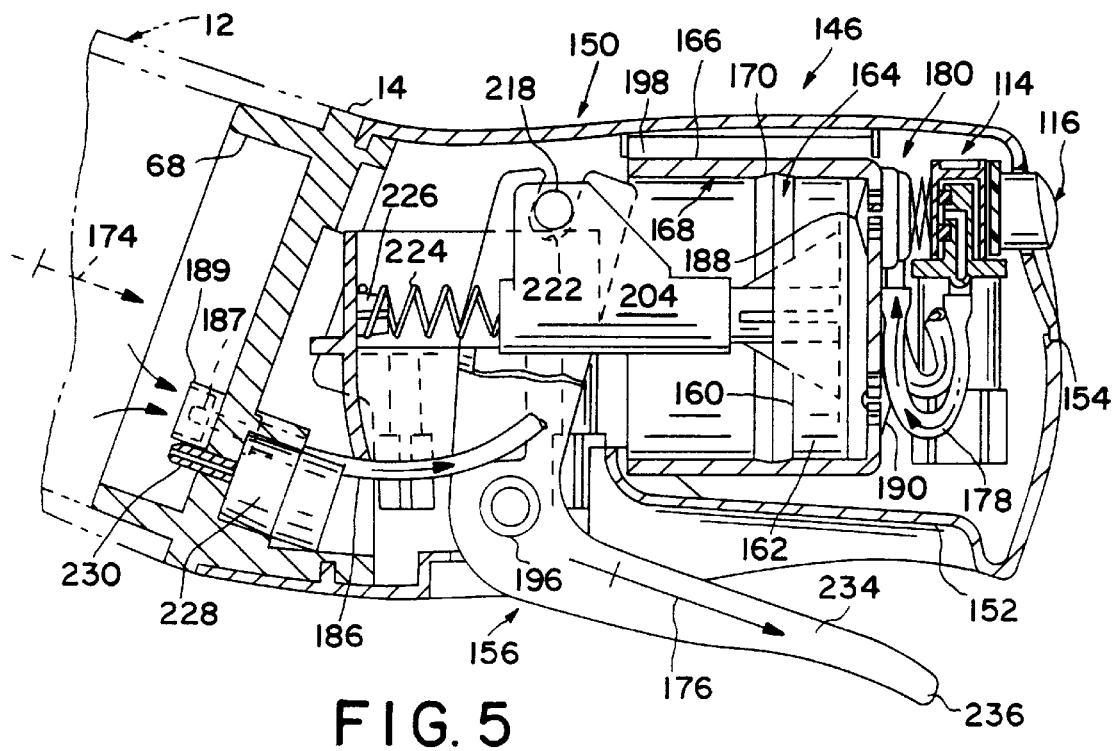
FIG. 5 is an enlarged, generally longitudinal cross sectional view, similar to that of present FIG. 3, but illustrating an exemplary manually operated vacuum pump arrangement and housing therefor in accordance with the subject invention, and illustrating an at rest position of a pump lever and pump piston thereof.
Figure 9:
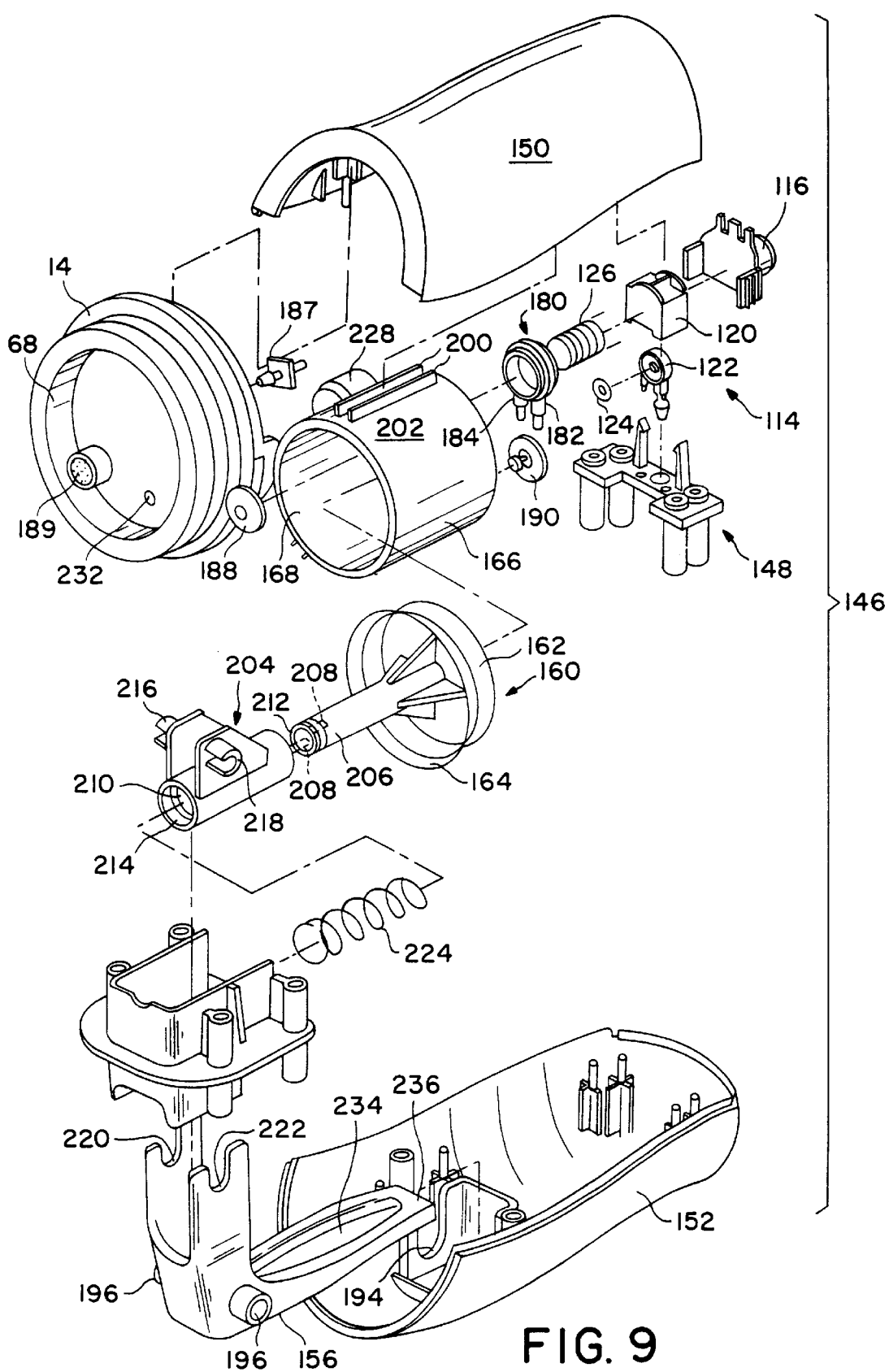
FIG. 9 is an exploded view, with component details, of the exemplary manually operated embodiment as otherwise represented in FIGS. 5 through 8.

Referring now to an exemplary embodiment of a manually operated arrangement generally 146 in accordance with the subject invention, a generally longitudinal cross sectional view of such an arrangement is shown in present FIG. 5, with an exploded, component detail view thereof illustrated in present FIG. 9. As referenced above, common features with prior embodiments are represented by corresponding reference character usage, without detailed repeating discussion herewith. For example, venting means generally 114 may be similarly utilized in the manually operated arrangements, with a substituting vent cradle generally 148 receiving various elements thereof in place of internal chassis 108.

Arrangement 146 (FIGS. 5, 5A, 6, 7, 8, and 9) primarily represents an exemplary self contained, manually operated male organ conditioning appliance in accordance with the subject invention (vacuum chamber 12 is represented only in FIG. 5 of such Figures). Arrangement 146 otherwise further includes a self contained manually operated pump housing having generally upper and lower members 150 and 152, respectively. In general, such housing members 150 and 152 may be joined along seal line 154 in various manners similar to those described above with reference to seal line generally 88 for the electric operated embodiment 66.

Figure 5A:
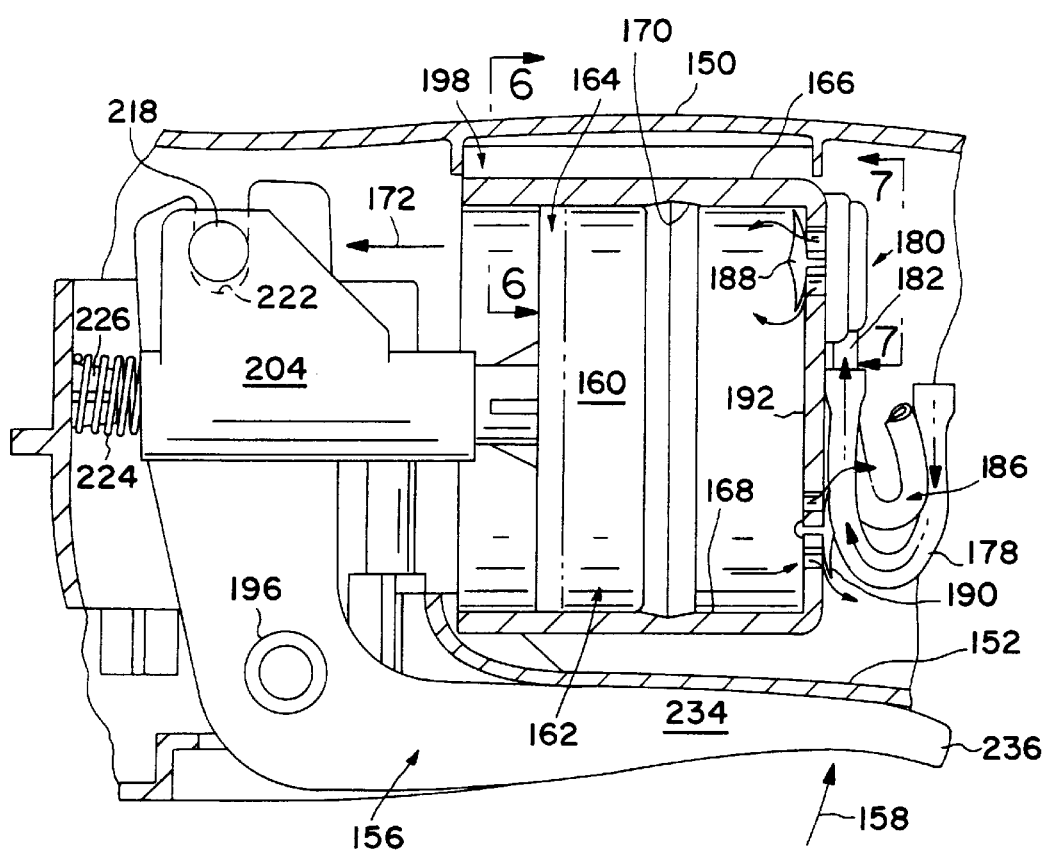
FIG. 5A is an enlarged cross sectional view of a portion of the exemplary manually operated embodiment illustrated in present FIG. 5, representing the pump lever and pump piston in an actuated state thereof.
Figure 6:
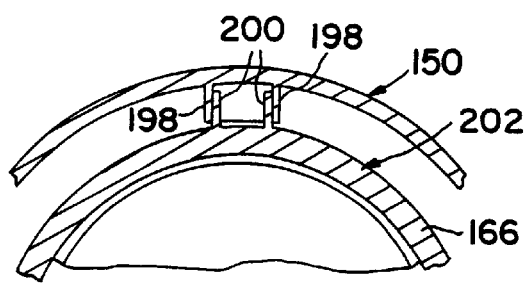
FIG. 6 is an enlarged cross sectional view of a portion of the pump cylinder and pump housing support thereof of the exemplary embodiment of present FIG. 5A, illustrated along the section line 6—6 indicated therein.

Arrangement 146 includes a vacuum pump with a pump lever generally 156 associated therewith. FIG. 5 illustrates such pump lever in an unactuated position thereof, while FIG. 5A illustrates pivoting of such lever generally in the direction of arrow 158 towards the housing component generally 152, into the actuated position thereof (FIG. 5A). By comparison, the illustration of present FIG. 5 represents an at rest position of component 156. As represented, such element 156 extends from pump housing generally 150/152 so as to be accessible for selective actuation by a user (i.e., depressing of lever 156 in the direction of 158). Since such depression activates the manual pump mechanism (as discussed below), the lever 156, in essence, forms pump actuation means external to the housing 150/152.

Still further, the vacuum pump of arrangement 146 includes a piston generally 160, having a piston head 162 with a circumferential resilient skirt generally 164.

As further illustrated, the vacuum pump of arrangement 146 further includes a cylinder generally 166 having a first predetermined inside diameter generally 168. A defined annular rest area generally 170 (see FIGS. 5 and 5A) is also formed on the inside diameter of cylinder generally 166. Such rest area 170 has a slightly enlarged inside diameter relative to the first predetermined inside diameter 168 of cylinder 166. As shown particularly by present FIG. 5, during its at rest position both for lever component 156 and piston head 162 with circumferential resilient skirt 164 thereof, skirt 164 is received in the slightly enlarged defined annular rest area generally 170 of cylinder 166.

In general, there is a slight taper (i.e., annular enlargement) of the inside diameter 168 of cylinder 166 (smaller to larger moving towards coupler 14). Regardless of such tapering, but particularly where it exists, it has been recognized as part of the present invention that a surprising compression set problem may occur with use of a resilient skirt such as element 164. In particular, the resiliency of such skirt 164 helps seal the piston element against the cylinder inside diameter for creating a vacuum during operation or manipulation of piston 160. However, if the vacuum pump arrangement of device 146 sets up for a period of time for nonuse, such as overnight, a resilient compression effect occurs such that some contact loss occurs between resilient skirt 164 and the inside diameter 168 of cylinder 166 as piston generally 160 goes through its vacuum inducing cycle (i.e., is drawn in the direction of arrow 172, FIG. 5A).

To counteract the above surprising compression set problem, the defined rest area generally 170 permits skirt 164 to retain at all times it adequate resiliency for fully properly contacting for effective vacuum seal against the inside diameter 168 of cylinder 166, despite any relatively lengthy period of nonuse thereof.

As represented by present FIG. 5, the pump housing generally 150/152 (similar to the illustration of present FIGS. 1 and 2) also is inclined at a predetermined angle relative to a longitudinal axis (generally 174 of present FIG.

5) of vacuum chamber 12. Similar to the previous discussion, such incline or predetermined angle may fall within a range, for example, such as from about 15 degrees to about 25 degrees in some instances, or from about 10 degrees to about 30 degrees in others. Thus, the mechanical handling and vacuum sealing advantages of the arrangement described in present FIG. 1 are also attributed to the mechanically or manually operated embodiment and arrangement 146.

An additional aspect of the embodiment of the arrangement of 146 is represented by present FIG. 5. As illustrated therein, pump lever 156 is mounted so as to be pivoted away from vacuum chamber generally 12. When situated on the relative bottom of the pump housing, the rest angle thereof (as illustrated) is generally reversed to that of the predetermined angle between the pump housing 150/152 and vacuum chamber longitudinal axis 174. Hence, the at rest position of pump lever 156 (along general axis 176 thereof) is generally parallel with longitudinal axis 174 of vacuum chamber 12.

As heretofore discussed, venting means generally 114 may likewise be provided with the embodiment of present FIG. 5, and make use of an external vent button 116. A user may then grasp the combined housing elements 150 and 152, with the user's fingers received around the bottom thereof for selectively actuating pump lever 156, with the thumb free to selectively actuate vent button 116, or with another finger being used for such operation.

During a venting cycle, a vent line 178 interconnects with, in effect, a double barbed junction box generally 180. Such hermetic junction box is shown in greater detail per view line 7—7 as indicated in present FIG. 5A. It is to be understood that air may flow in either direction in and through vent junction box 180, via connecting barbs or nipples 182 and 184 thereof. Junction nipple 182 interconnects with vent line 178 to venting means 114, while junction nipple 184 interconnects with a further tubing element 186 which interconnects via a barb 187 and filter 189 (see FIG. 5) to the interior vacuum chamber 12, for venting same.

Figure 7:
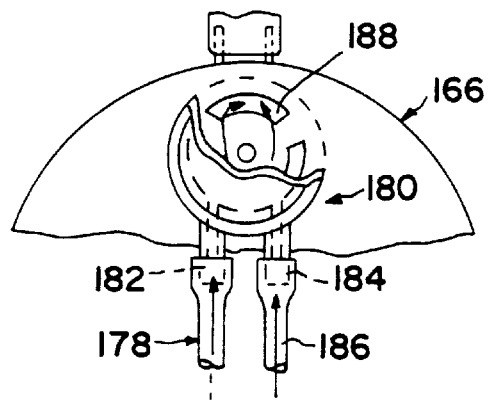
FIG. 7 is an isolated front elevational view (in partial cutaway) of a portion of the pump cylinder and certain air flow features of the exemplary embodiment of present FIG. 5A, as seen along the view line 7—7 indicated therein.

During venting, air flows within tubing 178 in the direction of the arrows as indicated in present FIGS. 5, 5A, and 7. Once entering hermetic junction box 180, the air flow within tubing 186 is opposite to the direction of the arrows within tubing 186 as illustrated in FIGS. 5 and 7. The solid line arrows in FIGS. 5 and 7 relative to tubing 186 illustrate the flow of air within tubing 186 as negative pressure or vacuum is created within vacuum chamber 12 during actuation of the pump arrangement of 146, as discussed hereinafter.

First, it is to be understood that cylinder 166 is provided with a pair of flapper valves 188 and 190, which function as follows. Such flapper valves may comprise mounted membranes, or relatively thin annular elements of resilient material (or their equivalents, e.g., spring loaded devices) which may become deflected by pressure variations. In the configurations illustrated, the flapper valves constitute one way valves, in that they permit air flow in one direction, but close to attempts at air flow in the opposite direction.

As variously illustrated in FIGS. 5, 5A, and 7, flapper valve 188 permits a flow of air into vacuum cylinder 166 (which is either from vacuum chamber 12 via tubing 186 or from venting means 114 via tubing 178, all via hermetic junction box 180). At the same time, flapper valve 190 constitutes an escape or discharge valve (FIG. 5A) for exhausting air from vacuum chamber 166 as piston head 162 pushes downwardly towards the bottom 192 of vacuum pump cylinder 166.

As further illustrated by the present Figures, the combined pump housing members 150 and 152 provide internal mounting elements 194 for establishing a pivot area via pivots 196 for pump lever generally 156. Only one of such cradle arrangements is visible in present FIG. 9, though a second such element 194 exists laterally from the illustrated element thereof. Similarly, an internal securement mechanism generally 198 (see FIG. 6) is provided to cooperate with a pair of projecting flanges 200 on an outside diameter 202 of pump cylinder 166. Such an arrangement locks cylinder 166 in place as to movement relative to the pump housing.

Still further, a linkage element generally 204 operatively interconnects between piston generally 160 and pump lever generally 156. As represented primarily in FIG. 9, a piston rod portion generally 206 of piston 160 has a pair of notches or central slot (dotted lines 208) to permit the end of piston shaft 206 to be received within annular or hollow interior 210 of linkage element 204. The projecting flange generally 212 on the end of piston shaft 206 is received and locked against stop or shoulder 214 of linkage 204, to keep shaft 206 from withdrawing from linkage 204. Shaft 206 can be released (if desired) by closing notches 208 till the shaft flange 212 can slip past stop 214.

Still further, the circular projecting elements 216 and 218 of linkage element 204 are correspondingly received within shoulders or bosses 220 and 222, respectively, of an upright or extending portion of pump lever generally 156, to provide a rotatable relationship between linkage generally 204 and pump lever 156. The resulting arrangement, as will be understood by those of ordinary skill in the art, causes the pivoting actuation movement of pump lever generally 156 (in the direction of arrow 158; FIG. 5A, and the return cycle opposite thereto) to be transmitted into longitudinal movement (in the direction of arrow 172; FIG. 5A, and the return direction opposite thereto) of piston generally 160 within the pump cylinder 166. Such movement is along an axis 172 (FIG. 5A) generally longitudinal to the pump housing formed by elements 150 and 152.

A biasing spring generally 224 is also supported within combined housing elements 150 and 152, for biasing the pump lever generally 156 and pump piston generally 160 into the respective illustrated rest positions thereof (present FIG. 5). In such rest condition, the piston resilient skirt generally 164 is receiving within the defined cylinder annular rest area generally 170, as discussed above. As will be understood by those of ordinary skill in the art, biasing spring 224 may be captured on one end by a support element generally 226 therefor, with the other end thereof received against linkage member 204 (with the biasing action of spring 224 transmitted through linkage element 204 to the piston 160).

FIGS. 5 and 9 further represent vacuum limiter means generally 228 which may be practiced in accordance with the subject invention. Vacuum limiter means 228 are operatively associated with the vacuum chamber 12 via connecting barb 230, and opening 232 in coupler 14. Vacuum limiter means 228 may comprise, for example, a spring actuated device, which opens once vacuum pressure within vacuum chamber 12 exceeds a predetermined amount, which would result in the flow of air through means 228 via barb 230 into vacuum chamber 12, to relieve the excessive negative pressure therein. With such an arrangement, a safety feature is provided to prevent excessive negative pressure within vacuum chamber 12, which could otherwise result in user discomfort.

Still further, it is to be understood that variations may be practiced in accordance with the subject invention. For example, the physical structure of the manually operated components of arrangement 146 may be varied. The pivotably mounted handle generally 234 of pump lever 156 may comprise various lengths from its pivot point 196 to the tip generally 236 thereof. For example, a length between such two points in a range of from about 2.5 inches to about 3.5 inches may be practiced. Likewise, the pump cylinder first predetermined inside diameter generally 168 may be varied in accordance with the subject invention, such as in a range of from about 1.5 inches to about 2.0 inches. A similar axial length of cylinder 166 (the direction along the length of arrow 172) may be practiced.

With the above-described arrangement, it is to be understood that air tubing such as 186, and the barbs and seals associated therewith, comprise a hermetically sealed air tubing means for interconnecting vacuum chamber 12 to the above-described manually operated vacuum pump.

With appropriate adjustment of all of the above sizes, it is to be understood that the capacity of such vacuum pump of the arrangement 146 combined with the mechanical advantage of the pump lever generally 156 thereof may be selected such that a negative pressure of up to 10 inches of mercury may be drawn via the above-described hermetically sealed air tubing means in as few as 10 complete strokes of the pump lever as actuated by a user. Other vacuum pump capacity variations may be practiced in accordance with the subject invention.

Figure 11:
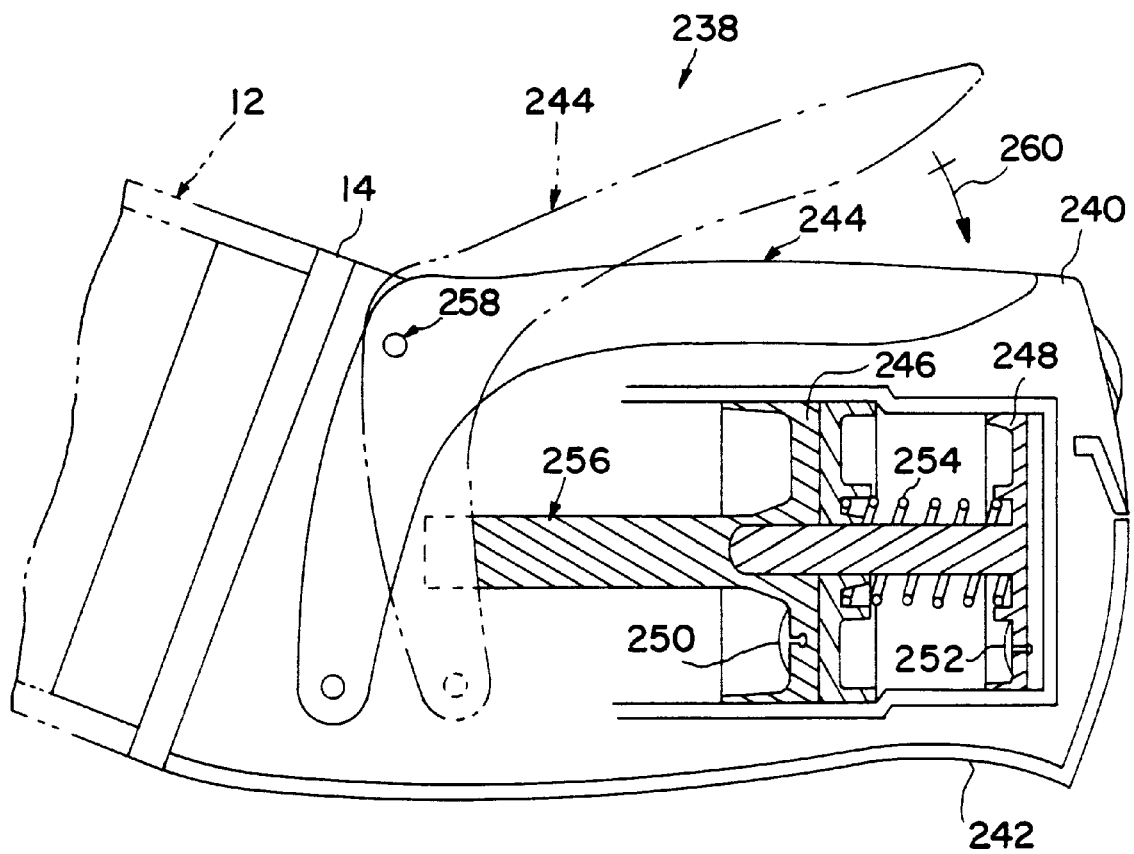
FIG. 11 is an enlarged generally longitudinal sectional view of an exemplary pump housing of a second embodiment of a manually operated vacuum pump arrangement and apparatus in accordance with the subject invention.
Figure 12:
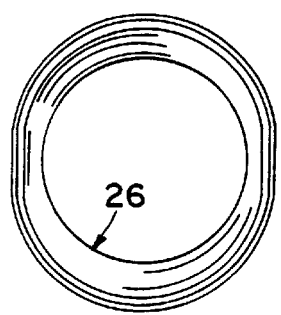
FIG. 12 is a generally end elevational view of a distal or second open end of an exemplary vacuum chamber in accordance with the subject invention.

Still further, it is to be understood that altogether different vacuum pump arrangements may be practiced with the subject invention, whether electric or manually actuated. For example, present FIG. 11 represents a second embodiment of a manually actuated arrangement generally 238. With such an arrangement, respective upper and lower housing components 240 and 242 may be provided in association with a coupler generally 14 at a predetermined angle (as above) relative to the longitudinal axis of vacuum chamber 12. However, instead of a pump lever mounted on the bottom side thereof, a top mounted pump lever generally 244 may be provided, with subsequent pivotable movement thereof as represented by the dash line and solid line positions of present FIG. 11.

Such FIG. 11 illustrates a generally longitudinal sectional view, diagrammatically representing a dual barrel inline pump mechanism having, for example, a pair of piston heads generally 246 and 248, and a pair of pump cylinder intake flapper valves 250 and 252, respectively. In such an arrangement, a single biasing spring 254 may be utilized, with the combined piston shaft 256 (actuating both pistons 246 and 248) interacting for actuation by pivoting of pump lever 244 about pivot point 258 thereof.

Still further, it will be understood that such pump lever 244 may be thumb actuated or otherwise, but still mounted so as to be pivoted away from a user's torso. With such top side mounting arrangement (FIG. 11), actuation pivoting of pump lever 244 is towards the combined housing elements 240 and 242, generally in the direction of arrow 260, as represented in present FIG. 11 (i.e., from the at rest dotted line position towards the actuated solid line position of pump lever 244).

With the foregoing arrangement of FIG. 11, it is to be understood that the at rest angularity of pump lever 244 adds to the predetermined angle relative to the angle between combined housing elements 240/242 and the axis of vacuum chamber 12, as opposed to being reversed thereof, as was the condition for the first manually actuated embodiment discussed above with reference, for example to FIG. 5.

As an additional aspect of the above-described manually operated embodiments, especially the embodiment of present FIG. 5 thereof, it is to be understood that the combined housing results in efficient cooperation in terms of internal support for the vacuum pump components. Accordingly, high reliability and efficient vacuuming operations result.

Likewise, for each of the above-described embodiments involving a pump housing or similar, the contoured shape thereof results in the upcurve grasping feature (for either manual or electric embodiments), for improved user friendliness and confident practice of the present embodiments of vacuum technology. The removable style of the vacuum cylinder relative to the pump housing also facilitates packing (for travel) or cleaning thereof.

It should be further understood by those of ordinary skill in the art that the foregoing presently preferred embodiments are exemplary only, and that the attendant description thereof is likewise by way of words of example rather than words of limitation, and their use does not preclude inclusion of such modifications, variations, and/or additions to the present invention, as would be readily apparent to those of ordinary skill in the art, the scope of the present invention being set forth in the appended claims.

What is claimed is:

1. A male organ conditioning appliance for the treatment of impotence, comprising:
    an elongated vacuum chamber, having a first open end with a size sufficient to permit introduction of a user's flaccid penis into said chamber, and a second open end for application of negative pressure to said chamber adequate so as to produce an erection in the user's flaccid penis, said vacuum chamber having a generally longitudinal axis therealong, and said chamber having a size that is sufficient to accommodate the user's erect penis;
    a combination self contained pump housing and chamber handle detachably secured to said vacuum chamber second open end for application of negative pressure thereto, said combined housing and handle having a generally longitudinal axis disposed at a predetermined angle in a range of from about 10 degrees to about 30 degrees relative to said vacuum chamber generally longitudinal axis so as to facilitate creation of a vacuum seal with the vacuum chamber first open end during use of such appliance, wherein the longitudinal axis of the vacuum chamber and the longitudinal axis of the combined housing and handle are non-parallel; and
    an elastomeric coupler for interfacing between said vacuum chamber second open end and said combination housing and handle, with said vacuum chamber removably received thereon to facilitate packing and cleaning of said appliance; and
    venting means, operatively associated with said combination pump housing and handle, and selectively actuated by the user, for selectively venting negative pressure in said vacuum chamber to facilitate removal of said appilance from the user's body.

2. An appliance as in claim 1, wherein said predetermined angle is about 20 degrees.

3. An appliance as in claim 1, wherein said combination housing and handle includes a battery operated pump and an external power switch for said pump, accessible for selective actuation by the user.

4. An appliance as in claim 1, wherein said combination housing and handle includes a manually operated pump with an external pump lever for said pump, accessible for selective actuation by the user.

5. An appliance as in claim 4, wherein said pump lever is mounted so as to be pivoted toward said combination housing and handle by the user.

6. An appliance as in claim 5, wherein said pump lever is pivotably mounted on an underside of said combination housing and handle, so as to be drawn inwardly to said combination housing and handle by the user's fingers grasped therearound.

7. An appliance as in claim 5, wherein said pump lever is pivotably mounted on a top side of said combination housing and handle, so as to be drawn thereto by a user's thumb grasped thereover.

8. An appliance as in claim 1, further including:
insert means, operatively associated with said vacuum chamber first open end, for selective introduction thereto by the user, for adjusting the size of said vacuum chamber first open end to facilitate user comfort and vacuum sealing at said vacuum chamber first open end during use of said appliance; and
resilient cincture band means for being selectively received about the vacuum chamber adjacent said first open end thereof, for user application to the base of the user's penis once an erection has been produced thereto with said appliance, for capturing such erection.

9. An appliance as in claim 8, wherein said insert means includes respective primary and secondary annular inserts, said secondary annular insert having a relatively smaller diameter than said primary annular insert for being received therein, for selectively further downsizing said vacuum chamber first open end, said secondary annular insert being recessed below the exposed surface of said primary annular insert such that said primary annular insert maintains sealing contact with a user's body during use of the appliance with the secondary annular insert in place.

10. An appliance as in claim 1, wherein:
said vacuum chamber first open end is generally circular and said second open end thereof is generally oval shaped, with said vacuum chamber transitioning between such two shapes along the length thereof; and
said elastomeric coupler has a generally oval shaped bayonet style mount for an interference fit of said elastomeric coupler with said vacuum chamber generally oval shaped second open end.

11. An appliance as in claim 1, wherein said elongated vacuum chamber has an enlarging taper from said first open end to said second open end.

12. A self contained, manually operated male organ conditioning appliance, comprising;
an elongated vacuum chamber, having a first open end adapted for introduction of a user's flaccid penis into said chamber, and a second open end for application of negative pressure to said chamber adequate so as to produce an erection in the user's flaccid penis, said vacuum chamber having a generally longitudinal axis; and
a self contained manually operated pump housing removably combinable with said vacuum chamber second open end, and including a vacuum pump therein with a pump lever operative with said vacuum pump and extending from said pump housing so as to be accessible for selective actuation by a user;
wherein said vacuum pump includes a piston having a piston head with a circumferential resilient skirt for sealing against a cylinder wall and creating a vacuum within such cylinder as the position of said piston is manipulated within such a cylinder; and said vacuum pump further including a cylinder having a first predetermined inside diameter and a defined annular rest area for said piston skirt, said rest area having a enlarged inside diameter relative to said first predetermined inside diameter of said cylinder, with said rest area receiving said piston resilient skirt whenever said piston is at an at rest position thereof, to prevent compression set of said resilient skirt so as to facilitate subsequent movement of said piston within said cylinder with continuing interference fit between said piston resilient skirt and the cylinder inside diameter after periods of nonuse of said vacuum pump.

13. An appliance as in claim 12, wherein said pump housing has an axis which is inclined at a predetermined angle within a range from about 15 degrees to about 25 degrees relative to the longitudinal axis of said vacuum chamber to facilitate improved sealing between the vacuum chamber first open end and the user's body.

14. An appliance as in claim 13, wherein said pump lever is mounted so as to be pivoted away from the vacuum chamber, and is situated on the bottom of said pump housing at an at rest angle generally reversed to said predetermined angle between said pump housing and said vacuum chamber longitudinal axis, such that the at rest position of said pump lever is generally parallel with the longitudinal axis of said vacuum chamber.

15. An appliance as in claim 14, further including venting means contained within said pump housing and having a vent actuation button externally mounted thereon, said venting means being operatively associated with said vacuum chamber so as to vent negative pressure therefrom when actuated.

16. An appliance as in claim 15, further including vacuum limiter means received within said pump housing and operatively associated with said vacuum chamber, for automatically limiting the amount of negative pressure achievable therein by operation of said vacuum pump.

17. An appliance as in claim 15, wherein:
said pump housing includes internal mounting elements for establishing respectively a pivot area for said pump lever and a securement mechanism for said cylinder so as to lock said cylinder in place as to movement relative to said pump housing; and
wherein said appliance further includes a linkage element operatively interconnecting between said piston and said pump lever, with a rotatable relationship with said pump lever, so as to transmit pivoting actuation movement of said pump lever into longitudinal movement of said piston within said pump cylinder, along an axis generally longitudinal to the pump housing; and
wherein said pump housing further includes therein a biasing spring for biasing said pump lever and said pump piston into respective rest positions thereof, with said piston resilient skirt received in said cylinder annular rest area.

18. An appliance as in claim 17, wherein:
said pump lever includes a pivotably mounted handle generally external to said pump housing, and having a length from the pivot point thereof to its end in a range of from about 2.5 inches to about 3.5 inches;
said pump cylinder has a first predetermined inside diameter and an axial length in a range of from about 1.5 inches to about 2 inches; and wherein said appliance further includes heremetically sealed air tubing means interconnecting said vacuum chamber to said vacuum pump, and wherein the capacity of said vacuum pump combined with the mechanical advantage of the pump lever are selected such that up to 10 inches of mercury vacuum may be drawn via said hermetically sealed air tubing means in about 10 complete strokes or fewer of said pump lever by a user.

19. A pump assisted vacuum therapy impotence treatment system with separable components to facilitate storage and cleaning thereof, said system comprising:

a vacuum chamber with opposing open ends and a generally longitudinal axis, with a first end thereof being generally circular and adapted for introduction of a user's flaccid penis, and with the second end thereof being generally oval shaped and adapted for introduction of negative pressure to said vacuum chamber, the generally oval shaped second end having a major diameter and a minor diameter which is smaller than the major dimaeter;

a coupler formed of resilient material, and having a generally oval shaped interference fit mount for sealing fit thereof with said vacuum chamber generally oval shaped second open end;

a pump housing having a predetermined contour, integrally secured with said coupler, and contoured so that the axis of said housing is at a predetermined angle to the longitudinal axis of said vacuum chamber;

a selectively operable vacuum pump received in said pump housing, and pump actuation means situated externally to said pump housing for producing negative pressure within said vacuum chamber whenever said vacuum chamber is sealed with said coupler; and venting means, operatively interacting with said pump housing, and selectively actuated by a user, for selectively venting negative pressure in said vacuum chamber to facilitate removal of said vacuum chamber from a user's body.

20. A system as in claim 19, wherein:

said vacuum pump comprises a battery operated or manually operated pump; and wherein said system further includes;

insert means, operatively combinable with said vacuum chamber first end, for selective introduction thereto by a user, for adjusting the size of said vacuum chamber first end to facilitate user comfort and vacuum sealing at said vacuum chamber first end during vacuum therapy use of said vacuum chamber; and resilient cincture band means for being selectively received about the vacuum chamber adjacent said first end thereof, for user application to the base of a user's penis once an erection has been produced thereto with said vacuum chamber, for capturing such erection.

21. A system as in claim 20, wherein said vacuum pump comprises a battery operated pump, and said pump actuation means comprises a power switch externally accessible on said pump housing; and wherein said predetermined angle between said housing and said vacuum chamber axes is about 15 to about 25 degrees.

22. A system as in claim 20, wherein said vacuum pump comprises a manually operated pump, and said pump actuation means comprises a pivoted pump lever externally accessible on said pump housing; and wherein said predetermined angle between said housing and said vacuum chamber axes is about 15 degrees to about 25 degrees; and wherein said system further includes vacuum limiter means operatively associated with said vacuum chamber for automatically limiting the amount of negative pressure created therein with operation of said vacuum pump.

* * * * *